US007591978B2

(12) United States Patent
Dwir et al.

(10) Patent No.: US 7,591,978 B2
(45) Date of Patent: Sep. 22, 2009

(54) SOLID PHASE TEST DEVICE FOR SIALIDASE ASSAY

(75) Inventors: Oren Shraga Dwir, Rehovot (IL); Tomer Keren, Rishon Le Zion (IL); Falk Fish, Tel Aviv (IL)

(73) Assignee: Inverness Medical Switzerland GmbH, Zug (CH)

( * ) Notice: Subject to any disclaimer, the term of this patent is extended or adjusted under 35 U.S.C. 154(b) by 264 days.

(21) Appl. No.: 11/502,192

(22) Filed: Aug. 10, 2006

(65) Prior Publication Data

US 2008/0038766 A1 Feb. 14, 2008

(51) Int. Cl.
*G01N 21/00* (2006.01)
(52) U.S. Cl. .......................................... 422/56; 435/18
(58) Field of Classification Search .................. 435/25, 435/18; 422/56
See application file for complete search history.

(56) References Cited

U.S. PATENT DOCUMENTS

| | | | |
|---|---|---|---|
| 4,499,185 A | 2/1985 | Skjold et al. | |
| 5,360,595 A | 11/1994 | Bell et al. | |
| 5,622,871 A | 4/1997 | May et al. | |
| 5,663,055 A | 9/1997 | Turner et al. | |
| 5,948,631 A | 9/1999 | Nagel et al. | |
| 6,512,100 B1 | 1/2003 | Johnson et al. | |
| 6,607,896 B1 * | 8/2003 | Millar et al. | 435/34 |
| 6,667,161 B1 | 12/2003 | Johnson et al. | |
| 6,753,189 B1 | 6/2004 | Narahara et al. | |
| 2003/0162240 A1 | 8/2003 | Johnson et al. | |
| 2003/0181691 A1 | 9/2003 | Johnson et al. | |
| 2004/0180393 A1 * | 9/2004 | Johnson et al. | 435/15 |
| 2007/0128589 A1 * | 6/2007 | Sanders et al. | 435/5 |
| 2007/0218132 A1 * | 9/2007 | De Simone | 424/468 |
| 2008/0038759 A1 * | 2/2008 | Keren et al. | 435/7.92 |

FOREIGN PATENT DOCUMENTS

| | | | |
|---|---|---|---|
| CN | 1850985 | * | 3/2006 |
| DE | 196 32 432 A1 | | 2/1998 |
| EP | 0 848 066 A1 | | 6/1998 |
| EP | 1 130 111 A2 | | 9/2001 |
| EP | 1 657 550 A1 | | 5/2006 |
| WO | WO 88/05912 | | 8/1988 |
| WO | WO00/55354 A3 | | 9/2000 |
| WO | WO 02/065122 A1 | | 8/2002 |

OTHER PUBLICATIONS

Myziuk L. et al. BVBlue Test for Diagnosis of BV. J of Clinical Microbiology 41(5)1925-1928, May 2003.*
Achyuthan K. Langmuir 20(6)2424-2428, 2004.*
Amsel et al., "Nonspecific vaginitis: Diagnostic Criteria and Microbial and Epidemiologic Associations." *The American Journal of Medicine* 74(1983): 14-22.
Wiggins et al. "Use of 5-Bromo-4-Chloro-3-Indolyl-α-D-N-Acetylneuraminic Acid in a Novel Spot Test to Identify Sialidase Activity in Vaginal Swabs from Women with Bacterial Vaginosis." *Journal of Clinical Microbiology.* vol. 38. No. 8. Aug. 2000. pp. 3096-3097.
Bradshaw et al. "Evaluation of a Point-of-Care Test, BVBlue, and Clinical and Laboratory Criteria for Diagnosis of Bacterial Vaginosis." *Journal of Clinical Microbiology.* vol. 43. No. 3. Mar. 2005. pp. 1304-1308.
Brochure for BVBLUE Test.
Fujii et al., "X-Neu5Ac: A Novel Substrate for Chromogenic Assay of Neuraminidase Activity in Bacterial Expression Systems." *Bioorganic & Medical Chemistry.* vol. 1. No. 2. 2003. pp. 147-149.
Myziuk et al., "BVBlue Test for Diagnosis of Bacterial Vaginosis." *Journal of Clinical Microbiology.* vol. 41. No. 5. May 2003. pp. 1925-1928.
Gossrau et al. "Azoindoxyl Methods for the Investigation of Hydrolases." *Histochemistry.* No. 57. 1978. pp. 323-342.
Gossrau et al. "5-Brom-3-indolyl-α-ketoside of 5-N-Acetyl-D-neuraminic Acid a New Substrate for the Light and Electron Microscopic Demonstration of Mammalian Neuraminidase" *Histochemistry.* No. 53. 1977. pp. 189-192.
Gossrau et al. "Tetrazolium Methods for the Histochemical Investigation of Hydrolases." *Histochemistry.* No. 58. 1978. pp. 203-218.
Gossrau et al. "Indoxyl Alfa-D-Galactoside as the Temporarily Last Substrate for Glycosidase Histochemistry. The Present State of the Art in Histochemical Glycosidase Research Using Indoxyl Glycosidas." *Folica Histochemica et Cytobiologica.* vol. 28. No. 3. 1990. pp. 129-144.
Lojda et al. "Enzyme Histochemistry. A Laboratory Manual." Springer-Verlag. 1979. pp. 138-139.
Spiegel et al. "Diagnosis of Bacterial Vaginosis by Direct Gram Stain of Vaginal Fluid." *Journal of Clinical Microbiology.* vol. 18. No. 1. Jul. 1983. pp. 170-177.
Nugent et al. "Reliability of Diagnosing Bacterial Vaginosis is Improved by a Standardized Method of Gram Stain Interpretation." *Journal of Clinical Microbiology.* vol. 29, No. 2. Feb. 1991. pp. 297-301.
Sobel. "Vaginitis." *The New England Journal of Medicine.* vol. 337. No. 26. Dec. 25, 1997. pp. 1896-1903.
Briselden et al. "Sialidases (Neuraminidases) in Bacterial Vaginosis and Bacterial Vaginosis-Associated Microflora." *Journal of Clinical Microbiology.* vol. 30. No. 3. Mar. 1992. pp. 663-666.
McGregor et al. "Bacterial Vaginosis is Associated with Prematurity and Vaginal Fluid Mucinase and Sialidase: Results of a Controlled Trial of Topical Clindamycin Cream." *Am J Obstetrics Gynecology.* vol. 170. No. 4. Apr. 1994. pp. 1048-1060.

(Continued)

*Primary Examiner*—Ralph Gitomer
(74) *Attorney, Agent, or Firm*—Merchant & Gould P.C.

(57) ABSTRACT

A solid-phase test device and a method for the detection of sialidase activity in a fluid sample. The test device includes a solid support provided with a pre-deposited dry form of a sialidase detecting composition. The sialidase detecting composition includes a sialidase substrate and a color-developing reagent. When the sialidase substrate is exposed to sialidase it yields an intermediate compound which reacts with the color-developing reagent to form a detectable color change.

20 Claims, 3 Drawing Sheets

OTHER PUBLICATIONS

Wiggins et al. "Mucinases and Sialidases: Their Role in the Pathogenesis of Sexually Transmitted Infections in the Female Genital Tract." *Sexually Transmitted Infections* (STI Online). vol. 77. 2001. pp. 402-408.

Olmsted et al. "Glycosidase and Proteinase Activity of Anaerobic Gram-Negative Bacteria Isolated from Women with Bacterial Vaginosis." *Sexually Transmitted Diseases*. vol. 30. Mar. 2003. pp. 257-261.

Smayevsky et al. "Vaginal Microflora Associated with Bacterial Vaginosis in Nonpregnant Women: Reliability of Sialidase Detection." *Infectious Diseases in Obstetrics and Gynecology*. vol. 9. 2001. pp. 17-22.

Form PCT/IB/326 for corresponding International Application PCT/IL2007/000993.

Form PCT/ISA/237 for corresponding International Application PCT/IL2007/000993.

International Search Report for corresponding International Application PCT/IL2007/000993.

* cited by examiner

SOLID PHASE TEST DEVICE FOR SIALIDASE ASSAY

BACKGROUND OF THE INVENTION

1. Field of the Invention

The present invention generally relates to enzyme assays and more specifically to a method and device for a dry format sialidase assay for the diagnosis of infectious diseases.

2. Discussion of the Related Art

The present invention discloses methods and devices for the detection of sialidase activity in fluid samples and in particular for the detection of sialidase activity in bodily fluids for the diagnosis of infectious diseases.

Sialidases, also known as neuraminidases, are the enzymes that catalyze the cleavage of terminal sialic residues from carbohydrate moieties of glycoproteins, glycolipids, and proteoglycans. Sialidases specific for varying ketosidic linkages perform many biological functions. They are found in viruses, bacteria, parasites, and vertebrates, including mammals. Sialidases are associated with many diseases. Bacterial and viral sialidases may act as pathogenic factors in microbial infections by processing carbohydrate moieties of glycoproteins and glycolipids on the host cell surfaces. Elevated sialidase activities in bodily fluids have been shown to be associated with bacterial and viral infectious diseases including bacterial vaginosis and influenza. In humans, abnormal production of sialidases is associated with diseases such as sialidosis and increased *Pseudomonas aeruginosa* infection in cystic fibrosis patients.

In particular, high levels of sialidase activity have been found in women having bacterial vaginosis, an abnormal condition of the vaginal ecosystem caused by a flora shift from the *lactobacillus* species present in normal conditions to overgrowth of a variety of aerobic and anaerobic vaginal bacteria, including *Gardnerella vaginalis, Bacteroides, Prevotella, Mobilincus* and *Mycoplasma* species. Bacterial Vaginosis (BV) is a common disease in reproductive-age women and is responsible for approximately one-third of all cases of Vulvovaginitis. BV is associated with gynecologic and obstetric complications including an increased risk for salpingitis, endometritis, pelvic inflammatory disease (PID), chorioamnionitis, premature rupture of membrane, and preterm birth. BV is also associated with higher susceptibility to sexually transmitted pathogens, including HIV. A number of studies have shown BV to be associated with elevated sialidase activity. Other studies have shown that direct sialidase assay on vaginal fluid may identify the BV syndrome. Correlation was also found between elevated sialidase activities and an increased risk of preterm birth and low weight infants, suggesting that a sialidase activity test may predict adverse pregnancy outcome in women diagnosed with BV. The correlation found between elevated sialidases and pre-term birth also suggests that sialidase might be responsible for this complication by causing degradation of the protective mucus gel. The higher susceptibility to sexually transmitted pathogens might also be associated with the enzymatic degradation of the mucus gel that otherwise helps protect against such pathogens.

Conventional methods for diagnosing BV rely on an expert assessment and laboratory tests. Currently, there are two standard methods for diagnosing BV, the Amsel clinical criteria test and the Gram stain Nugent score. The Amsel criteria require the presence of at least three of four clinical signs set forth by Amsel et al. (Amsel et. al. *Am. J. Med.* 74:14-22, 1983). The alternative, more objective, method is to use a Gram stained evaluation of vaginal smears with the Nugent criteria or score (Nugent et al. *J Clin Microbiol* 29:297-301, 1991). This method scores the smears in a standardized manner by quantification of some of the cell types present designated as *Lactobacillus, Gardnerella vaginalis, Bacteroides* and *Mobilincus* 'morphotypes'. The relative proportions of bacterial morphotypes give a score between 0 and 10. A score of $\leq 3$ is normal, 4-6 is intermediate and $\geq 7$ is BV positive. However, complete evaluation of BV by the Amsel criteria or by Gram-stained smears is time consuming. Moreover, it requires skilled personnel and microscopic capabilities, which are not available in many of the physician offices or other clinic settings attended by women with BV. As a result, samples need to be sent to a laboratory and results are further delayed, or more often, laboratory tests are not performed and diagnosis is based on clinical signs only, which may be misleading. There is therefore a need for a rapid point-of-care diagnostic test for BV which will aid in quick diagnosing BV while the patients are still in clinic and will allow starting appropriate treatment with no delay.

Recently, a new point-of-care BV test, distributed under the name BVBlue®, has been developed. The BVBlue® is a two-step liquid-phase chromogenic test, based on the detection of increased sialidase activity in vaginal fluid. The test kit contains a solution of a sialidase substrate, referred to as IBX-4041 which when exposed to bacterial sialidase undergoes chemical reaction to yield sialic acid and a compound referred to as IBX-4050. The test procedure involves the immersion of vaginal swab in the IBX-4041 solution to let it stand for 10 minutes. A drop of a 1M NaOH is then added to generate a blue or green color upon a positive result and a yellow color when the result is negative. The BVBlue test was evaluated by a number of studies and has been shown to be a useful point-of-care diagnostic tool for BV, exhibiting good sensitivity and specificity as compared with Amsel criteria and Nugent score (Myzuik et al., *J. Clin. Microbiol.,* 41:1925, 2003), Bradshaw et al, *J. Clin. Microbiol.,* 43:1304, 2005). While the BVBlue® provides a liquid phase sialidase point-of-care test, there is still a continuous need for other simple point-of-care tests for BV detection, and in particular for a one-step dry format sialidase assays, preferably of the strip format type.

Accordingly, it is the general object of the present invention to provide a simple, one-step, dry format assay for the detection of sialidase activity in a fluid sample.

More specifically it is the object of the invention to provide a rapid point-of-care test for the diagnosis of infectious disease associated with sialidase activity It is a further object of the present invention to provide a test as set above for the diagnosis of bacterial vaginosis.

A further object of the invention is to provide a test as set above in a lateral flow format for facilitating analyte concentration and signal enhancement.

It will be appreciated that while the above and following description focuses on BV detection, the present invention is not limited to the detection of BV sialidases. Rather, the method and devices of the invention may be applied for the detection of sialidases of any other origin including bacterial, viral, protozoa or human origin and for the diagnosis of other infectious sialidase-related diseases, including influenza, *T. cruzi* infection and *Pseudomonas aeruginosa* infection, as well as for human sialidase-associated disorders such as sialidosis. For example the disclosed invention may be used as a first screen for the detection of influenza virus.

SUMMARY OF THE PRESENT INVENTION

The present invention provides an improved method and devices for detecting sialidase activity in bodily fluids as a diagnosis tool for infectious diseases.

One aspect of the invention is a solid-phase test device for the detection of sialidase activity in a fluid sample. The device comprises a solid support provided with pre-deposited dry form of a sialidase detecting composition comprising a sialidase substrate and a color-developing reagent, wherein the sialidase substrate when exposed to sialidase yields an intermediate compound, which reacts with the color-developing reagent to form a detectable color change. The composition may further comprise a surfactant for further intensifying the signal.

In accordance with a special embodiment, the device of the invention is configured as a strip for a lateral flow sialidase assay. The strip comprises a first flow matrix, a second flow matrix and an absorbent pad sequentially arranged on a non-absorbing solid support, wherein liquid flows from the first, sample receiving, flow matrix toward the absorbent pad. The sialidase detecting composition is movably bound in a re-suspendable manner on the first flow matrix such that it carried on by the liquid. The permeation rate of the liquid through the first, sample receiving, matrix is higher than the permeation rate through the second matrix. Preferably the first matrix is a fiber glass, a filter paper or a polymeric matrix of relatively large pores while the second matrix is a nitrocellulose or a nylon membrane of lower porosity. The first and second matrices are arranged so as to form an overlapping interface zone therebetween, preferably of about 1 to 5 mm length in the direction of the liquid flow. The interface zone is the signal zone where the at least one product of the reaction between the intermediate compound and the color-developing reagent accumulates. The zone impregnated with the sialidase detecting composition, comprising the sialidase substrate, the color developing reagent and optionally a surfactant, may overlap the sample receiving zone or may be located upstream of the sample receiving zone. The zone impregnated with the sialidase substrate may overlap with or be located upstream of the zone impregnated with the color-developing reagent.

Another aspect of the invention is a method for performing a rapid one-step sialidase assay for detecting sialidase activity in a fluid sample, the method comprising: providing a test device of the invention, applying a fluid sample to the device, and observing appearance of a color change, wherein appearance of a distinguished color change indicates presence of sialidase in said fluid sample. The test device may be a spot test device, whereby a drop of the fluid sample is placed on said test device or a strip adapted for a lateral flow assay constructed according to any of claims 10 to 23, the strip comprising a first flow matrix and a second flow matrix; wherein said exposing comprises loading the fluid sample and a running buffer on a receiving zone of the strip and wherein said observing comprises observing appearance of a signal line at an interface between the first and the second flow matrices.

The devices and method of the invention may be applied as a diagnostic tool for the detection of infectious diseases associated with abnormal sialidase activity, by applying a sample of bodily fluid, such as for example a vaginal discharge sample, where sialidase activity indicates the presence of Bacterial Vaginosis pathogens.

BRIEF DESCRIPTION OF THE DRAWINGS

The present invention will be understood and appreciated more fully from the following detailed description taken in conjunction with the drawings in which.

DETAILED DESCRIPTION OF THE PREFERRED EMBODIMENT

Figure 1:
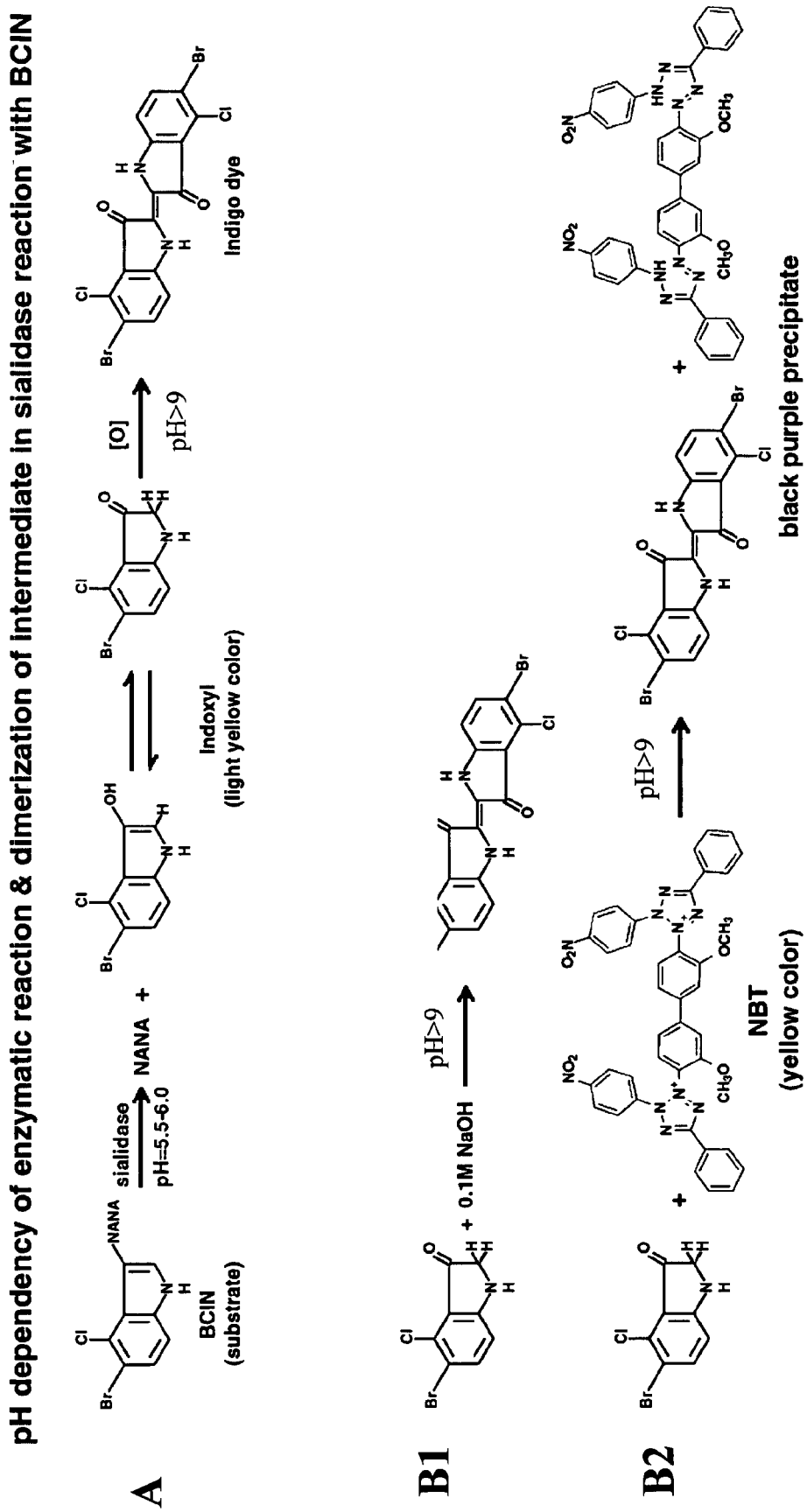
FIG. 1 is a reaction scheme of the chemical reaction of a sialidase substrate (BCIN) with NBT

The present invention provides a method for the performance of a one-step detection of sialidase activity in a dry format for the diagnosis of infectious diseases associated with sialidase activity. The invention further provides test devices for detecting sialidase activity, including a lateral flow test strip of a novel structure.

The invention exploits the use of a sialidase detection composition comprising a sialidase substrate and a color-developing reagent, both pre-deposited on a solid support. The sialidase substrate and the color-developing reagent are selected so that upon hydrolysis, the sialidase substrate yields an intermediate compound, which further reacts with the color-developing reagent to form a visible or otherwise detectable color change. The sialidase detecting composition may further comprise a color intensifier, preferably a surfactant.

The sialidase substrate comprises a sialic moiety ketosidically linked to a non-sialic moiety (also referred to as the aglycon portion). Upon hydrolysis the ketoside link cleaves to yield a sialic acid or a derivative thereof and a non-sialic compound. Preferably, the aglycon portion of the sialidase substrate is an indoxyl or a substituted indoxyl and the color-developing reagent is an oxidizer, which oxidizes the indoxyl to form an indigo dye. More preferably, the color-developing reagent is a tetrazolium salt. Upon reduction, the tetrazolium ion is transformed to the intensely colored formazan, thus significantly enhancing the signal intensity. The sialic acid may be N-acetylneuraminic acid (abbreviated NANA or Neu5Ac) or a derivative thereof. U.S. Pat. Nos. 6,512,100 and 6,667,161 assigned to IBBEX Inc. disclose a variety of sialidase substrates suitable for the present invention. In particular suitable for the invention are the compounds belonging to the group of the structure designated general structure II, in which the non-sialic moiety is a substituted or a non-substituted indoxyl.

In order to develop and optimize a rapid one-step test, sialidase activity was first assayed in a series of wet tests, using 5-bromo-4-chloro-3-indolyl-α-D-N-acetylneuraminic acid (BCIN) as the substrate. BCIN is a well known chromogenic neuraminidase substrate, first synthesized by Fujii et al. (Bioorg. Med. Chem., 1: 147-149, 1993). When subjected to sialidase, the colorless BCIN (1) is hydrolyzed to yield N-acetylneuraminic acid (Neu5Ac) and halogenated indoxyl (2), which under oxidizing conditions undergoes dimerization to form the indigo dye, 5,5'-dibromo-4,-4'-dichloroindigo (3), as shown in the following:

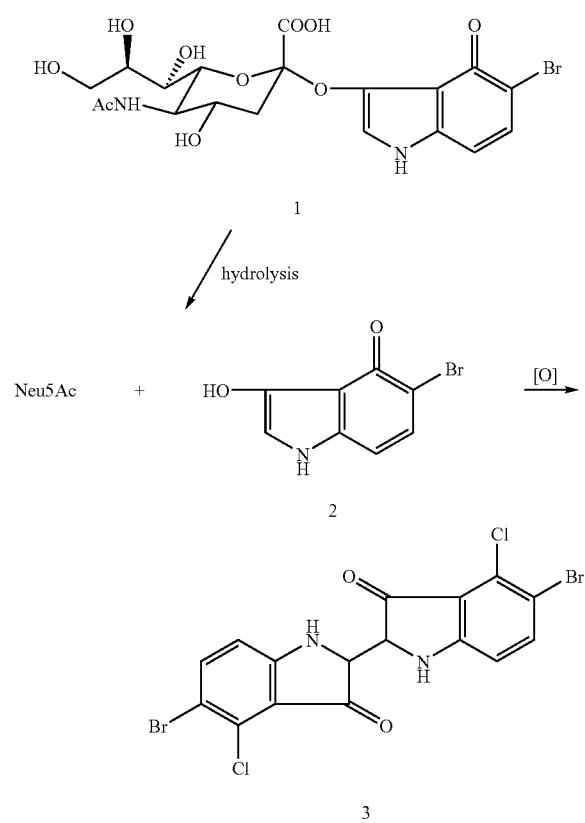

The sialidase activity was tested for vaginal swabs extracts that had been independently screened for BV by Nugent score. A standard sialidase test was established using the BCIN substrate with different concentrations of *B. fragilis*, a BV-related bacterium which express sialidase. Samples of purified sialidase and of *C. albicans* (sialidase negative) were used as controls. The results obtained for the vaginal swabs extracts were scored by comparison to the results obtained by the standard sialidase test under the same conditions. An initial series of tests had been performed in which the swab extracts samples were incubated for 30 minutes at 37° C. Under these conditions, a complete correlation was found between sialidase activity and Nugent scoring, confirming the validity and accuracy of sialidase assay as a method for diagnosing BV.

Next, a series of tests, still in wet format, was carried at ambient temperature for studying the effect of various parameters, including pH, on the incubation time, in order to find optimal conditions under which signal appearance time is minimized. The optimal pH for sialidase catalytic activity is reported to be in the range of 5.5-6.0. The tests carried during the present study confirmed this value. However, it was also found that at this acidic pH, the spontaneous dimerization of indoxyl is very slow, showing no change of color at a desired time period of less than 10 minutes. When the reaction pH is adjusted to basic pH (>9.0), spontaneous dimerization is immediate but the enzymatic reaction is slow, leading to the same results, namely a long time of incubation (about 30 minutes) is required before a change of color is noticeable. The pH optima of the sialidase catalyzed BCIN hydrolysis and indoxyl spontaneous dimerization are shown in scheme A of FIG. 1. No optimal pH was found under which the overall reaction to yield the indigo dye proceeds fast enough to give a signal in less than 10 minutes.

While it is known to accelerate spontaneous oxidation of indoxyl by alkalization (see scheme B1 in FIG. 1), addition of basic solution is not feasible in a one-step assay where all reagents should be present in one composition. An alternative route was therefore chosen of adding an oxidizing agent into the substrate solution, which can co-exist with the substrate and which will oxidize the indoxyl immediately as it is formed. Various oxidizers, including various tetrazolium salts were checked for their effect on the appearance time and intensity of signals for samples of vaginal swabs extract and of the standard sialidase solutions mentioned before. The oxidizer, which serves as a coloring-developing reagent, is preferably colorless or of a light color so as not to obscure the signal by a colored background. The addition of tetrazolium salts to the sialidase substrate was found to significantly reduce the time of signal appearance. Tetrazolium salts are known as highly sensitive color indicators of enzymatic redox reactions and are very common oxidizers in staining applications. The hydrolysis of the BCIN by sialidase results in a powerful reducing product, i.e. indoxyl, which reduces the light color tetrazolium salts to the deep color formazans. Thus, the addition of tetrazolium salt not only facilitates the development of the indigo color but results in an additional distinguished color change due to the formation of formazan. The reaction between indoxyl and tetrazolium salt is shown in scheme B2 of FIG. 1 for nitro blue tetrazolium (NBT). Other tetrazolium salts were found to show similar effect, including tetra nitro blue tetrazolium (TNBT), p-iodo nitro tetrazolium (INT) and 3,3-[(Phenylamino)carbonyl]-3,4-Tetrazolium-Bis(4-methoxy-6-nitro)benzenesulfonic acid hydrate.

A sialidase detection composition of the invention comprising BCIN and tetrazolium salt was tested for samples of purified sialidase, positive and negative sialidase bacteria and vaginal swabs, as described above, in various dry assay formats including spot test formats and flow-through formats to give a dark brown-purple precipitate in the presence of sialidase. Addition of surfactants was found to further intensifies the signal. It was also found, that the signal intensity is significantly enhanced at interface areas between matrices of different permeability.

A lateral flow test strip of a novel structure was designed for carrying out the sialidase assay of the invention, wherein a dry form of the sialidase detection composition is movably bound in the sample receiving zone of the strip while the signal capture zone is formed at the interface between two matrices of different flow-through permeability.

It is known to use a lateral flow formats for accumulating analyte at a capture zone, thus enhancing the signal intensity and increasing sensitivity. Strips for lateral flow assays typically comprise a sample receiving zone at one end, an absorbent pad serving as a wick at the opposite end and a capturing zone located therebetween. According to the prior art, the capturing zone in non-chromatographic strips is constructed by immobilizing a substance specific to the analyte. Prior art strips may further comprise a labeling zone, located between the sample receiving zone and the capturing zone, where a label compound is movably bound. The lateral flow assay is carried out by applying the sample containing the analyte at the sample receiving end and allowing it to travel along the strip by capillary action, to pick up the label compound when present, and further downstream to be captured and accumulated by the immobilized substance at the capture zone. In accordance with the preferred embodiment of the present invention for carrying out the sialidase activity assay, there is provided a novel strip for lateral flow assays wherein all the detection reactants are movably bound to the strip and wherein the capture zone is formed at the interface between two sequentially ordered solid flow matrices. The term "flow matrix" as used throughout the application refers to any liquid permeable transport material that allows for liquid flow therethrough, including materials such as nitrocellulose, nylon, rayon, cellulose, paper, glass fiber and silica or any other porous, fibrous or bibulous material. The flow matrix is preferably configured as a substantially planar rectangular strip. The flow matrix material can be pretreated or modified as needed.

Figure 2A:
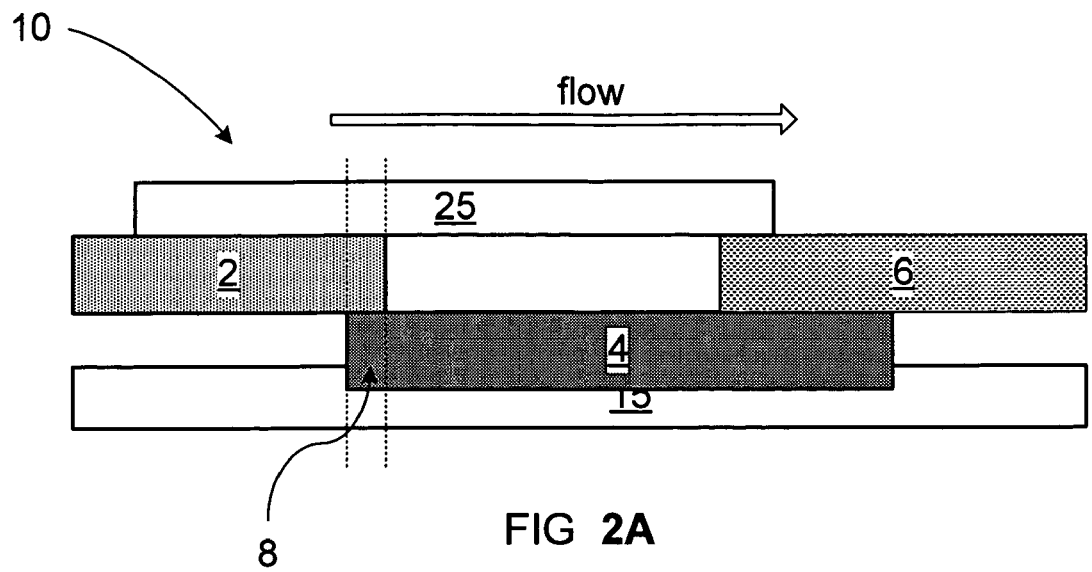
FIGS. 2A and 2B are an exploded side view and a top view, respectively, of a lateral flow strip constructed in accordance with a preferred embodiment of the invention.
Figure 2B:
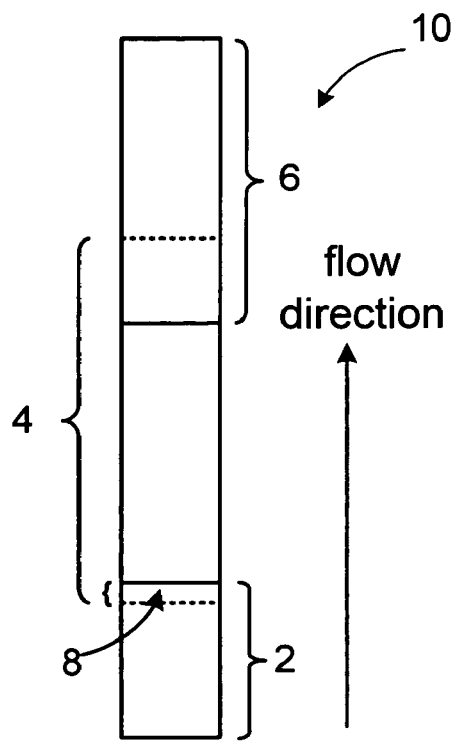

Referring to FIG. 2, there is shown the novel strip of the invention, generally designated 10. Strip 10 comprises two flow matrices, a sample receiving pad 2 and a reaction membrane 4 sequentially ordered on backing layer 15 so as to form an interface zone 8 of 1-5 mm where receiving pad 2 and membrane 4 overlap. Interface zone 8 is the signal zone where change of color appears upon positive reaction. Pad 2 and membrane 4 are selected to have different porosity and consequently different permeation rates. Preferably, the permeation rate of the sample through pad 2 is higher than its permeation rate through membrane 4. Pad 2 may be a glass fiber (GF), a filter paper or any other known in the art filtration or mesh medium of relatively large pore size, preferably a fibrous material. Matrix 4 is preferably, but is not limited to, a nitrocellulose (NC) or a nylon membrane. Preferably, the pore size of membrane 4 is in the range of from about 0.22 μm to about 15 μm. The strip further comprises an absorbent pad 20 and a top laminate 25 configured to cover membrane 4 and to partially cover pad 2 and absorbent pad 6, leaving a portion of pad 2 uncovered where the sample is to be applied and most of pad 6 exposed. Absorbent pad 6 is made of a bibulous material, such as a cellulose or filter paper, so that liquid is drawn through pads 2 and 4 and accumulates in absorbing pad 6. The size and shape of the pad 6 is chosen according to the volume of liquid used in the assay. Back and top laminate 15, 25 are non-absorbing films. Preferably, both film 15 and 25 are transparent or translucent films for allowing viewing the signal from both sides of the strip. However, using a white film on one side and a transparent film on the other side can increase the contrast of the signal zone in certain applications.

A dry form of the sialidase detection composition of the invention is movably bound on sample receiving pad 2. The composition components, namely the sialidase substrate, the color developing reagent and optionally a color intensifier, may be pre-deposited together in the same region of pad 2, or each of the components may be pre-deposited in a confined area of pad 2. When pre-deposited in confined areas, the region provided with the sialidase substrate is preferably located upstream of the color-developing reagent region.

Figure 3A:
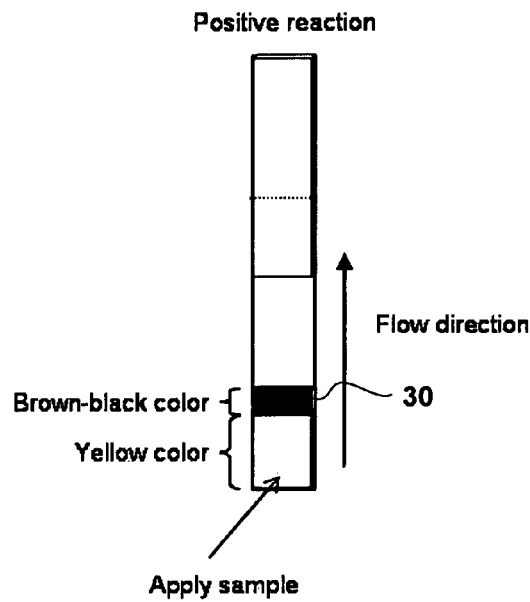
FIGS. 3A and 3B are schematic illustrations of a positive signal and a negative signal, respectively, obtained on a lateral flow strip of the invention.
Figure 3B:
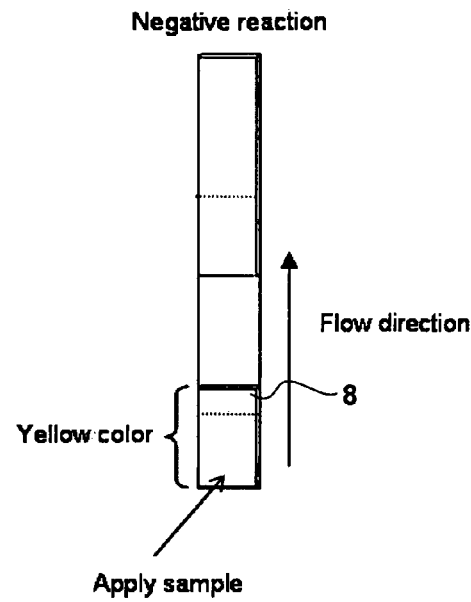

To perform a test, a sample and a running buffer are loaded on the exposed end of pad 2. The sample may be added to the running buffer beforehand to be loaded as one solution or alternatively, the running buffer may be loaded after the sample is spotted. As the sample solution moves along the strip, the pre-deposited composition is re-suspended in the solution to be mixed and react with the sample components as it along with the sample. Thus, in the presence of sialidase, the sialidase substrate undergoes hydrolysis to yield the intermediate non-sialic compound, which further reacts with the color-developing reagent to yield the intensely colored products. The colored products accumulate at the overlapping interface between sample receiving pad 2 and reaction membrane 4, where their flow slows down to give rise to a clear distinguished signal line. Referring to FIG. 3, a positive result is indicated by the appearance of a dark distinguished line 30 at signal zone 8 (FIG. 3A) while a negative result is indicated by absence of such a line at the signal zone.

It will be realized that the locations of the sample receiving zone, the sialidase substrate zone and the color-developing zone on the first flow matrix (i.e., on pad 2) may overlap as shown above or may comprise separate zones. Thus, the sample receiving zone may be located upstream of the sialidase substrate zone and the color-developing zone. Likewise, the sialidase substrate zone may overlap with or be located upstream of the color-developing zone.

The lateral flow strip of the invention may be used in a qualitative manner to give positive/negative answer corresponding to the presence or absence of sialidase in a test sample. In accordance with this embodiment, the strip may be incorporated into a lateral flow device provided with a receiving port for loading the sample at least one transparent window at the signal zone, thus providing a simple self-contained sialidase detecting device which requires no additional equipment. A reference may be added with a calibrated color intensity scale to make a semi-quantitative measurement by matching the signal intensity to the calibrated scale. Alternatively, the strip may be read by an instrument, such as, but not limited to, spectrophotometer, scanner, densitometer, reader, or camera, to give a quantitative result. Since, as mentioned before, the signal can be viewed from both sides of the strip, it allows for measuring both the absorbance and the reflectance of the signal.

It will be appreciated that while the use of the novel strip of the invention is described hereinabove in association with a sialidase assay, the strip is not limited to sialidase assays only, but rather it may be exploited for the detection of other enzymes with the required modifications. A more detailed description of the strip as well as possible uses and method of fabrication appear in a co-pending application titled "A Test Strip for Lateral Flow Assays", filed on the same date and assigned to the same assignee of the present invention, the full content of which is incorporated herein by reference. It will be also appreciated that the method and device of the invention are not limited to sialidase originating from BV pathogens. Rather, the sialidase assay of the invention may be used for the detection of sialidase originating from any source.

The following detailed examples are given for the sake of illustration only and are not intended to limit the invention to what is described therein.

EXAMPLE 1

Preparation of Sialidase Test Strip

A. Preparation of NBT-Impregnated Sample Pads

Glass fiber filters (Millipore, GFCP0010000, 10 mm×10 cm) were soaked in NBT solution for 30 minutes in the dark at room temperature. The soaked glass fiber filters were placed on a blotting paper to remove excess fluids and then transferred to drying oven for 15 minutes at 50° C. The dried NBT-impregnated glass fiber filters (sample pads) were stored dried and dark in a dry room (RH 5-10%) at room temperature.

B. Card Assembly

A test card was assembled according to the scheme in FIG. 2:

1. A 43×250 mm piece of clear plastic film with a release liner protected adhesive, serving as the back laminate, designated 15 in FIG. 2, (ARcare 8876, Adhesive Research, Limerick, Ireland) was placed on top of a worktable. The release liner was peeled to expose the adhesive side of the tape.

2. The reaction membrane (Nitrocellulose HF18004, Millipore, SA3J154101, 25×300 mm or Biodyne B, PALL, BNBZF3RT, 25×300 mm or Biodyne PLUS, PALL, ZNXG3R, 25×300 mm) was attached on top of the adhesive side of the back cover, 8 mm from the lower end.
3. The NBT-impregnated sample pad (prepared as in section A) was attached on top of the lower side of the back cover with 2 mm overlap on top of the reaction membrane.
4. The absorbent pad (Gel blotting paper, S&S, GB003, 21×300 mm) was placed on top of the upper side of the back cover with a 12 mm overlap on top of the reaction membrane.
5. The release liner of top laminate film (ARcare 7759, Adhesive Research, Limerick, Ireland) was peeled to expose the adhesive side and the film was attached, with the adhesive facing done, on top of the reaction membrane, with overlaps on top of the sample pad and absorbent pad.

The card was cured over-night in a dry room (RH 5-10%) at room temperature in the dark. Following curing, the card was trimmed to 4 mm width strips using an automated die cutter.

C. Impregnation of BCIN on the Strip Sample Pads

1 µl of BCIN solution was added on top of the sample pad and allowed to dry for 15 minutes at 37° C.

EXAMPLE 2

Running of Tests with Sialidase Test Strips

The strips constructed as described in example 1 above, were tested for sialidase activity with samples of sialidase producing bacteria: *Bacteroides fragilis*, sialidase negative bacteria: *Lactobacillus plantarum* and with purified sialidase.

Figure 4:
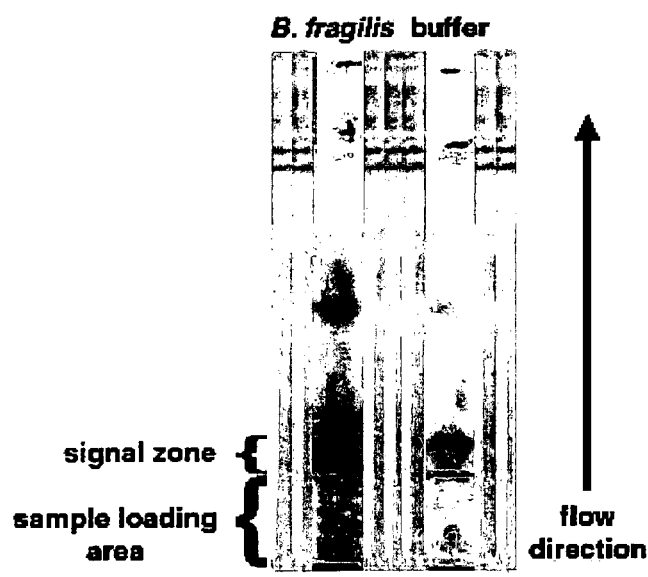
FIG. 4 shows exemplary results obtained with a lateral flow strip of the invention; the left strip shows results obtained with a sample of *B. fragilis*; the right strip shows a control run with running buffer; the strips were scanned after 10 minutes incubation.

To start the test, 25 µl of sample was loaded onto the sample pad of the strip. The signal of positive sialidase reaction, a brown-purple color, was accumulated at the interface between the two different matrices (sample pad and the reaction membrane), namely the signal zone. Negative control (where no sialidase present) showed a yellow background at the signal zone. For each test the signal appearance time was recorded. The strips were observed up to 30 minutes. FIG. 4 shows exemplary results obtained with a sample of *Bacteroides fragilis* (left strip) and with running buffer (right strip) as a negative control.

The color change at the signal zone could be observed visually and was assigned "+" values (see Table 1) alternatively or in addition, the color can be detected and measured by an electro-optical instrument. The signal appearance time from the loading of the sample to the test strip and the intensity of the signal at 10 minutes are shown in the table. The results are summarized in following Table 1.

TABLE 1 results obtained by the sialidase test strip

| Sample (25 µl) | Time of signal appearance (minutes) | Signal intensity after 10 minutes* |
|---|---|---|
| *B. fragilis* $5 \times 10^6$ cells | 2 | ++++ |
| *B. fragilis* $2.5 \times 10^6$ cells | 3 | +++ |
| *B. fragilis* $10^6$ cells | 6 | ++ |
| *B. fragilis* $5 \times 10^5$ cells | 8 | + |
| *B. fragilis* $2.5 \times 10^5$ cells | — | − |
| *B. fragilis* $10^5$ cells | — | − |
| *L. plantarum* $5 \times 10^6$ cells | — | − |
| Purified sialidase 5 units | 1 | ++++ |
| Purified sialidase 1 units | 1 | ++++ |
| Buffer | — | − |

*Relative signal intensity: Very strong (++++), strong (+++), medium (++), weak (+) and no signal (−).

EXAMPLE 3

Clinical Samples (Vaginal Swabs)

47 clinical samples were tested to test the clinical relevance of the Sialidase test strip for the diagnosis of Bacterial Vaginosis BV. Vaginal discharge samples were obtained from volunteers at the Genitourinary Infections unit of the Wolfson Medical Center, Holon, Israel. Vaginal discharges were collected by a physician using a sterile swab (552C, Copan, Italia). The swab heads (tips) were placed in 2 ml screw-cap tubes and kept at 4° C. until use. The vaginal swabs were washed by adding 300 µl of running buffer in to the tube and by vortexing for 1 minute to elute the secretions from the swab and to achieve a homogenous sample. For each vaginal swab a diagnosis for BV was done using Gram staining and Nugent scoring. From the 300 µl swab wash, 25 µl were taken for the test. The test was done as described above for culture samples. Table 2 summarizes the result of 47 vaginal swabs washes that were diagnosed for BV and tested with the Sialidase test strip.

TABLE 2 results obtained by sialidase test strip for of 47 vaginal swabs diagnosed for BV by Nugent score

| 47 Swabs Tested | BV Positive | BV Negative |
|---|---|---|
| Nugent Score | 22 | 25 |
| Sialidase Test Strip | 22 | 25 |

The sensitivity and specificity of the Sialidase test strip are 100%. The results summarized in Table 1 and 2 clearly demonstrate that the proposed sialidase test strip could be used for the diagnosis of BV Materials and Preparation of Solutions NBT solution 2 mg/ml NBT (Nitro blue tetrazolium chloride, N-8100 Biosynth AG, Switzerland), 5% sucrose (5553810, Frutarom, Haifa, Israel), 0.1% $MgCl_2$ (1200310, Merck, Darmstadt, Germany) in 50 mM MES (M-8250, Sigma-Aldrich, Rehovoth, Israel) buffer pH 6.0; NBT solution with Surfynol-440 2 mg/ml NBT (Nitro blue tetrazolium chloride, N-8100 Biosynth AG, Switzerland), 5% sucrose (5553810, Frutarom, Haifa, Israel), 0.1% $MgCl_2$ (1200310, Merck, Darmstadt, Germany), 0.5% surfynol-440 (2,4,7,9 tetramethyl-5-decyne-4,7-diol ethoxylate 1.75EO/OH, Aldrich, 461180) in 50 mM MES (M-8250, Sigma-Aldrich, Rehovoth, Israel) buffer pH 6.0; BCIN Solution 35.3 mg BCIN (5-Bromo-4-chloro-3-indolyl-α-D-N-acetyl-neuraminic acid sodium salt, B4666, Sigma) in 1 ml double distilled water; Running Buffer 0.5% PEG (PolyEthyleneGlycol-15000, Merck, 819003), 0.5% BSA (01200050, Seracare, Calif., USA), 0.1% Tween 20 (Sigma, P-5927), 0.1% $MgCl_2$ (Merck 1200310) in TBS (Tris buffer saline) pH 7.8.

Bacterial Cultures

Sialidase producing bacteria: Culture of *Bacteroides fragilis* (ATCC #23745) $10^7$ cfu/ml. 25 µl of sample was prepared by dilutions of the culture in running buffer to the following number of cells: $5 \times 10^6$, $2.5 \times 10^6$, $1 \times 10^6$, $5 \times 10^6$, $2.5 \times 10^5$ and $10^5$. Sialidase negative bacteria: Culture of *Lactobacillus plantarum* (ATCC #14917) $10^9$ cfu/ml. 25 µl of sample with $5 \times 10^6$ cells was prepared by dilution of the culture in running buffer. Purified Sialidase Purified recombinant bacterial sialidase from *Clostridium perfringens* (P0720L, Neuraminidase), was obtained from New England Biolabs, MA., USA). 25 μl samples were prepared by dilutions of the purified sialidase in running buffer to the following levels: 5 units and 1 unit per sample.

It will be appreciated by persons skilled in the art that the present invention is not limited to what has been particularly shown and described hereinabove. Rather the scope of the present invention is defined only by the claims which follow.

The invention claimed is:

1. A solid-phase test device for the detection of sialidase activity in a fluid sample, configured as a strip for a lateral flow assay, the device comprising a first flow matrix, a second flow matrix and an absorbent pad sequentially arranged on a non-absorbing solid support in fluid communication with each other to allow flow of fluid from said first flow matrix through said second flow matrix into said absorbent pad, wherein a sialidase detecting composition comprising a sialidase substrate and a color-developing reagent is movably bound in a re-suspendable form on said first flow matrix, and wherein said sialidase substrate when exposed to sialidase yields an intermediate compound which reacts with said color-developing reagent to form a detectable color change.

2. The test device of claim 1 wherein said first flow matrix and second flow matrix are of different permeation rates, the permeation rate through the first flow matrix being higher than the permeation rate through the second flow matrix.

3. The test device of claim 1 wherein said first flow matrix is a glass fiber matrix or a filter paper.

4. The test device of claim 1 wherein said second flow matrix is a nitrocellulose membrane or a nylon membrane.

5. The test device of claim 1 wherein said first flow matrix and second flow matrix are arranged so as to form an overlapping interface zone therebetween.

6. The test device of claim 5 wherein said overlapping interface zone is of about 1 to 5 mm length in the direction of liquid transport.

7. The test device of claim 1 wherein the first flow matrix is a glass fiber or a polymeric membrane and said second flow matrix is a nitrocellulose or nylon membrane.

8. The test device of claim 1 wherein at least one product of the reaction between said intermediate compound and said color-developing reagent is an insoluble color precipitate.

9. The test device according to claim 8 wherein said precipitate is accumulated at an interface between the first and second flow matrices.

10. The test device of claim 1 wherein the first flow matrix comprises a first zone impregnated with the sialidase substrate, a second zone impregnated with the color-developing reagent and a third zone for receiving a sample.

11. The test device of claim 10 wherein said first, second and third zones are overlapping.

12. The test device of claim 10 wherein said third zone is located upstream of said first and second zones.

13. The test device of claim 10 wherein said first zone is located upstream of said second zone.

14. The test device of claim 1 wherein said fluid sample is a vaginal discharge sample.

15. The test device of claim 1 wherein the detectable color change forms a signal line at an interface between the first and the second flow matrices.

16. The test device of claim 1 wherein the reaction between said intermediate compound and said color-developing regent is an oxidation-reduction reaction.

17. The test device of claim 1 wherein said sialidase substrate comprises a sialic moiety linked to a non-sialic moiety by a ketoside bond and wherein said non-sialic moiety is an indoxyl or a derivative thereof.

18. The test device of claim 17 wherein said sialic moiety is N-acetylneuraminic acid or a derivative thereof.

19. The test device of claim 1 wherein said sialidase substrate is 5-bromo-4-chloro-3-indolyl-α-D-N-acetylneuraminic acid or a salt thereof.

20. The test device of claim 1 wherein said composition further comprises a surfactant.

* * * * *